Figure 1:
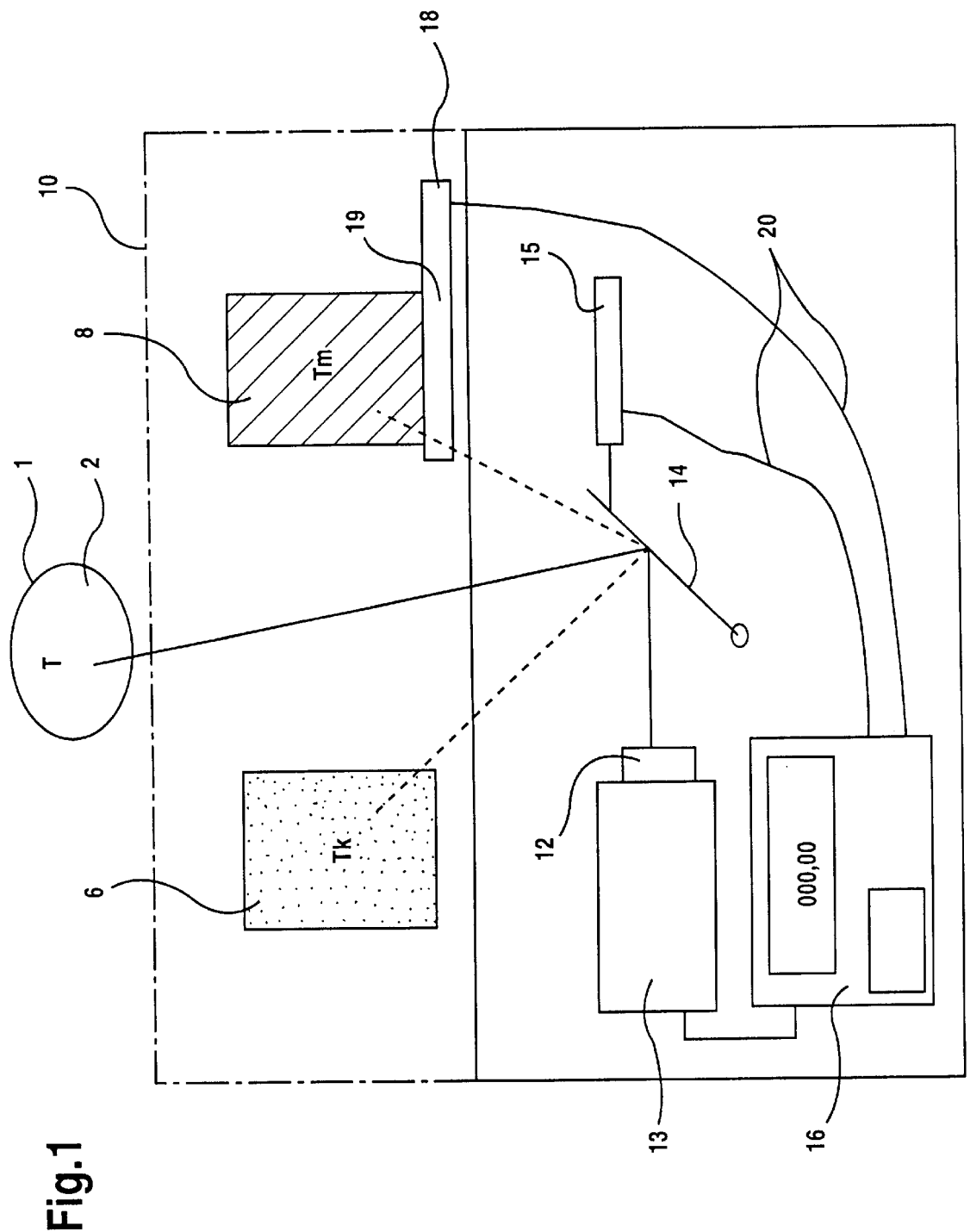

United States Patent
Takala

[11] Patent Number: 6,076,960
[45] Date of Patent: Jun. 20, 2000

[54] METHOD AND APPARATUS FOR METERING EVAPORATION

[76] Inventor: Jouni Kalevi Takala, Pellonmäenraitti 3As 10, FIN-53920 Lappeenranta, Finland

[21] Appl. No.: 09/147,377

[22] PCT Filed: Jun. 12, 1997

[86] PCT No.: PCT/FI97/00371

§ 371 Date: Dec. 11, 1998

§ 102(e) Date: Dec. 11, 1998

[87] PCT Pub. No.: WO97/47960

PCT Pub. Date: Dec. 18, 1997

[30] Foreign Application Priority Data

Jun. 13, 1996 [FI] Finland ................................ 962457

[51] Int. Cl.⁷ .............................................. G01N 25/62
[52] U.S. Cl. ............................................ 374/28; 374/54
[58] Field of Search ................................ 374/54, 16, 27, 374/28, 45; 73/53.01, 29.01, 73

[56] References Cited

U.S. PATENT DOCUMENTS

| | | |
|---|---|---|
| 3,195,343 | 7/1965 | Paulik et al. ............................. 374/14 |
| 3,831,435 | 8/1974 | Hoffman et al. ............................. 73/73 |
| 4,409,834 | 10/1983 | Kethley ..................................... 73/336 |
| 4,599,889 | 7/1986 | Pateras Pescara de Castelluccio .......................... 73/23 |
| 5,581,015 | 12/1996 | Kiesow .................................. 73/29.01 |
| 5,692,832 | 12/1997 | Selby ..................................... 374/54 |
| 5,844,125 | 12/1998 | Pillion .................................. 73/29.01 |
| 5,847,263 | 12/1998 | Springmann et al. ................. 73/29.01 |

Primary Examiner—G. Bradley Bennett
Assistant Examiner—Gail Verbitsky
Attorney, Agent, or Firm—Arent Fox Kintner Plotkin & Kahn PLLC

[57] ABSTRACT

The invention relates to a method and an apparatus for metering evaporation. According to the invention the temperatures ($T_k$, $T_m$, T) are defined for a comparing piece (6) in an essentially non-evaporating state, for a comparing piece (8) in an essentially evaporating state and for the metered object (1). Based on a mutual comparison of the obtained temperature values ($T_k$, $T_m$, T) the evaporation index (n) dependent on the amount of liquid evaporated will be defined.

10 Claims, 1 Drawing Sheet

METHOD AND APPARATUS FOR METERING EVAPORATION

BACKGROUND OF THE INVENTION

The present invention relates to a method, for defining evaporation and particularly to a method for evaluating the amount of evaporation. The present invention further relates to a device arrangement, in order to realize the inventive method.

Metering evaporation is important in many different fields, such as in connection with various researches in plant physiology or in industrial sectors dealing with evaporation, such as different sectors in process-, chemical engineering- or paper industry.

Description of Related Art

Prior methods have included, for instance, when metering evaporation from the surfaces of leaves of plants, using electronic evaporation metering devices, that require a so-called filter through metering device. Such a filter through metering device is manually attached on the surface on a leaf. The filter through metering device creates an air proof space, that contains a gas, whose moisture is metered with electronic hydrometers per se known in the art, and this metering gives the amount of evaporation.

The weakness of this solution has been, though, that it has been troublesome and time consuming to perform and also that the required equipment has been complicated and expensive. It has not been possible to meter evaporation without touching and/or covering the object. Touching and/or covering disturbs in most cases at least to some extent the natural evaporation of the metered object, which can result in inaccuracies in the obtained metering results, thus making the method unreliable. Attaching the filter through and thence also the metering is troublesome to perform. This is especially the case with fragile plants leaves or other similar objects that cannot support weight or objects with an uneven surface. In some cases it would also be important to obtain an essentially large metering surface, which has not been possible with the prior art techniques.

SUMMARY OF THE INVENTION

The object of the present invention is to abolish the disadvantages of the prior art and to provide an innovative solution for defining the amount of evaporation. The inventive solution provides a method and a device for metering the amount of evaporation, which device is easy to use, quick, reliable and adaptable to several different tasks of defining the amounts of evaporation.

It is a further object of the present invention to provide a method and a device for carrying out that method, which enable defining the amount of evaporation without touching and/or covering the surface of the metered object.

An additional object of the invention is to provide a method and an equipment for carrying out the method, in which the metering situation is essentially stable and the number of variables as low as possible.

An additional object of the invention is a method and a device for metering the amounts of evaporation on essentially large surfaces.

It is an object of the invention to further provide a method and means for carrying out the method, with which the metering result can be presented in the desired unit stating the amount of evaporation.

The invention is based on the realization that the amount of evaporation can be defined by comparing the evaporation temperatures of objects in different states, that is by utilizing the physical dependency between the evaporation temperature and the amount of evaporation, according to which a surface from which liquid evaporates becomes cooler in proportion to the amount of evaporation.

According to a preferred embodiment of the present invention the method includes the step of defining or metering the surface temperature of three pieces or objects situated in the same metering environment. The metered pieces consist of a piece, whose amount of evaporation has to be defined and at least two special comparing pieces, whose physical characteristics essentially correspond to the physical characteristics of the metered piece.

One of the comparing pieces is essentially in a so-called non-evaporating state or dry. This piece will further on be referred to as the dry control. Another comparing piece is in an essentially evaporating state or contains a large amount of the liquid to be evaporated or is saturated with it. This piece will be referred to in the following as the wet control. According to a preferred embodiment the amount of liquid/time unit evaporated by this wet control is also metered in the metering environment in question unless it is sufficiently accurately known otherwise. With the aid of said controls the metering situation can be stabilized in relation to the environment, since all three metered objects are situated in the exactly same environment. An especially stable situation can be obtained by executing the meterings essentially simultaneously.

The obtained temperature values are compared to each other and the factor dependent on the amount of evaporation or the so called evaporation index is defined by their ratio. By means of this it is possible to define the amount of liquid evaporated by the metered piece for instance as a value of amount/surface area unit, such as $mlcm^{-2}$. The obtained value is based on a physical phenomenon according to which a surface evaporating liquid becomes cooler in relation to the amount of evaporation/mass.

According to a preferred embodiment the amount of liquid evaporated by the wet control by time unit is also metered, unless it is known otherwise sufficiently accurately. The metering can be carried out e.g. by weighing the loss in weight per time unit or by metering the consumption of the amount liquid to be evaporated.

According to one embodiment the metering of the temperature is performed without touching the surface of the metered piece, e.g. with a suitable heat wave camera or with a measuring infrared beam. The metering of especially large areas, such as relatively large land areas, can also be performed by satellite mapping. The temperature can naturally be metered also from the object surface with suitable metering devices, such as temperature sensors.

The comparing and calculation operations according to the invention are preferably performed with suitable data recording and data processing equipment, such as a microprocessor. One example is a microcomputer and a portable microcomputer is considered an especially advantageous means for this purpose.

Remarkable advantages are obtained with this invention. The metering of the amount of evaporation can be performed quickly and reliably in an environment suitably stabilized according to this invention with a per se simple equipment and method. The metering can also be performed without the need to touch the surface of the metered piece. Several objects can be metered simultaneously. The same method and equipment can be applied to various types of evaporation meterings in various types of environments.

In the following the present invention and the other objects and advantages thereof will be described by way of an example with reference to the annexed drawings, in which similar reference characters throughout the various figures refer to similar features. It should be understood that the following description of an example of the invention is not meant to restrict the invention to the specific forms presented in this connection but rather the present invention is meant to cover all modifications, similarities and alternatives which are included in the spirit and scope of the present invention, as defined by the appended claims. It is also noted herein that by term metered object all such articles, objects, pieces, surfaces etc. are meant, in connection which there exists a need for determining the amount of liquid they evaporate.

BREIF DESCRIPTION OF THE DRAWINGS

FIG. 1 presents a simplified schematic view of an embodiment of the present invention.

FIG. 2 presents the metered object 1, the surface temperature on the surface 2 of which is T. In addition, the dry control 6 and the wet control 8, whose surface temperatures are $T_k$ and $T_m$ respectively, are presented.

The metering equipment 10, surrounded by a broken line, is equipped with thermometry means 12 that in this example include a spot metering long wave infrared thermometer 13, a movable or rotatable mirror 14, and a repeater motor 15. An essentially rapid rotation of the mirror 14 is obtained by using the motor 15, so that the meter 13 can read the temperatures from the surfaces of all three objects 1, 6, 8 in an essentially short period of time through the mirror 14. It should be noted, though, that the thermometry means 12 can be of another design, such as a heat wave camera or a temperature detector and that the mirror 14 and the repeater motor 15 are by no means necessary for the realization of this invention. Further, it may be necessary to create a suitable arrangement for observing the background temperatures/the environment temperature in order to further improve the metering accuracy.

Figure 1 also shows a means 18 for metering the amount of liquid evaporated by the wet control 8. In the example the means 18 includes weighing equipment 19, so that the amount of liquid evaporated is obtained as decrease in weight per time unit. Alternatively, the consumption of the amount of liquid evaporated by the wet control 8 can be metered. The wet control 8 can be, if needed, prepared for instance in a laboratory or it may be done industrially so that any known method or means for metering evaporation can easily be used as metering means 18 for the evaporated liquid, which various means are included in the present invention.

All the means of equipment 10, such as thermometry means 12 and evaporation metering means 18 are operationally connected to a data processor 16, for instance with conducting wires 20. The data processor 16 is preferably in the form of a microcomputer, and even more preferably in the form of a portable microcomputer. The processor 16 includes a suitable algorithm for collecting and comparing the received temperature values T, $T_m$, $T_k$ and for receiving other necessary parameters, such as the information on the amount of liquid evaporated by the wet control 8. The device 16 is adjusted to generate from the received values a result that gives the ratio of the liquid evaporated by the metered object 1 in relation to the controls, that is the so-called evaporation index. The amount of liquid evaporated by the object 1 may after this be converted with the processor 16 to be presented e.g. as a volume per surface area unit and/or per time.

The liquid saturated wet control 8 has a maximum evaporation and the dry control 6 has a minimum evaporation and accordingly the temperature $T_m$ of control 8 corresponds to the lowest and the temperature $T_k$ of control 6 corresponds to the highest possible temperature to be achieved in the atmosphere in question. The metered, evaporating object 1 settles, due to the above mentioned physical reasons, by its temperature T, between these or equals with one of them. The temperature of the metered object 1 is proportional to the amount of its evaporation in a corresponding state. Thence also the temperatures of the three (or more) physically similar objects in the same environment are correlated with the amounts of evaporation of these objects. This proportionality can be described by a ratio or the evaporation index n, which is between 0–1 (or 0–100%), in which case the complete evaporation receives the value 1 (or 100%) and the complete non-evaporation receives the value 0 (or 0%).

The evaporated amount can be derived from the measured temperatures. The evaporation index n describing the relative amount can be obtained as follows:

$$n = \frac{T - T_m}{T_k - T_m}, \text{ where:}$$

$T_k$ = the temperature of the dry control $T_m$ = the temperature of the wet control $T$ = the measured temperature of the object $n$ = the evaporation index (the ratio).

The index FIGURE n obtained is always between 0 . . . 1, when, as shown above with the value n=0 there is no evaporation in the object and with the value n=1 there is complete evaporation in the object or the evaporation of the object 1 completely equals the evaporation of the liquid saturated wet control 8.

The exact amount of evaporation per surface area unit of the wet control 8 is known for instance as a value ml/min/cm². This known or measured amount of evaporation of the wet control 8 is multiplied by the obtained evaporation index n, so that the exact value for the evaporation per surface area and/or time unit of the object 1 is obtained and the formula can be written as follows::

$$\frac{T - T_m}{T_k - T_m} \times S_m = H, \text{ where:}$$

$S_m$ = the consumption of liquid by the wet control per time unit/surface area $H$ = the evaporation of the object per surface area and time unit, for instance ml/cm²/s.

By adjusting the processor 16 so that it will automatically perform the above mentioned steps, the value for the amount of evaporation will be obtained in the desired form as a result. It is to be notified that the obtained amount of evaporation can be given as a value of any system and/or unit of measures or be transformed into such after the index value n has been generated. It must further be understood that certain conditions may require certain correcting factors, but their addition to the formulas above will not alter the spirit of the invention.

In the following, in order to further clarify the general idea and the advantages of the invention, one embodiment of the invention, that utilizes the long wave infrared camera, will be described.

With the methods of the prior art it is difficult to measure the surface temperatures of several objects in such a way that different objects could be controlled and calibrated with each other. When measuring with an infrared camera or beam it is difficult to obtain the exact real surface temperature. With the inventive method it is easy to measure relative temperature differences and these differences are obtained with high accuracy and from several different objects simultaneously if necessary.

A metering system based on infrared well applies to the implementation of the invention. Several different objects can be placed in the image of the infrared camera and/or the image or the beam can be controlled with mirrors (see FIGURE). Both controls and the metered object or objects may be seen in the same image. Since in this method it is only necessary to meter relative temperature differences, it gives the exact ratio which in turn yields the exact value for the evaporation of the metered object.

Temperature differences due to the calibration of the camera etc. will not affect the metering result, since as a result the method gives the relative value for objects in the same state and with corresponding physical characteristics.

With the invention, an equipment and a method that essentially improve metering of the amount of evaporation have thus been obtained. The inventive solution is easy and economical to realize, but it gives reliable metering results for different metering objects.

It must be remarked that the examples of the embodiments of the invention presented above do not limit the scope of protection of the invention presented in the claims. With the aid of the preceding explanation and the drawings it will be obvious for one of ordinary skill in the art to use the inventive method and device for example simultaneous metering of several objects. In this case common controls can be used or separate controls may be adjusted for each metered object, but all the objects and controls can still be metered with one equipment and essentially simultaneously. In addition, there may be more controls than two/the metered object. The liquid saturation rate of the controls can also completely differ from dry/completely saturated. The information obtained from the equipment 10 can be utilized in other ways, too, than as a number value. In this case for instance in industrial processes and devices it will give the basis for an automatic control of an actuator apparatus operationally connected to the equipment 10 so that its parameters are changed in the desired way in proportion to the obtained information on the amount of evaporation.

What is claimed is:

1. A method for metering the amount of evaporation, comprising the steps of:

defining the temperature ($T_k$) of a comparing piece (6) in a substantially non-evaporating state, defining the temperature ($T_m$) of a substantially liquid saturated, evaporating comparing piece (8), defining the temperature (T) of metered object (1), and defining the evaporation index (n) dependent on the amount of liquid to be evaporated obtained as a ratio of comparison between (T) and (Tm) and (Tk) and (Tm).

2. A method according to claim 1, wherein the amount of evaporation of the liquid saturated evaporating comparing piece (8) is also defined, whereupon the evaporated amount per surface area unit of the object (1) will be derived from the evaporation index and said amount of evaporation.

3. A method according to claim 1, wherein the defining of the temperature (T) of the object (1) is done without touching the surface (2) of the metered object (1).

4. A method according to claim 1, wherein the defining of the evaporation index (n) comprises the steps of dividing the temperature difference between the evaporating piece (8) and the metered object (1) with the temperature difference between the evaporating piece (8) and the comprising pieces (6) and (8) in the non-evaporating state.

5. A method according to claim 1, wherein the temperature metering will be performed essentially simultaneously in the object (1) and the pieces (6) and (8) situated in essentially similar surroundings.

6. An apparatus (10) for metering evaporation of an object (1) to be evaluated, comprising:

a first comparing piece (6) in a non-evaporating state, a second, liquid saturated evaporating comparing piece (8), means (12) for metering the temperatures of the said object (1) and said comparing pieces (6, 8), and means (16) for comparing the obtained temperature values (T, $T_k$, $T_m$) and for deriving an evaporation index (n) proportional to the amount of evaporation on the basis of said comparison.

7. An apparatus according to claim 6, further comprising means (18) for metering the amount of evaporation of said evaporating comparing piece (8), said means being preferably adjusted to meter the consumption of the amount of liquid evaporated by the comparing piece or to weigh its loss in weight per time unit.

8. An apparatus according to claim 6, wherein the means (12) for metering the temperature of the surface (2) of the metered object (1) are adjusted to meter the temperature without touching the surface (2) of the object (1), these means comprising advantageously an infrared thermometer (13) or a heat wave camera.

9. An apparatus according to claim 6, wherein it is adjusted to meter the amount of evaporation of several objects.

10. An apparatus according to claim 6, further comprising means (16) operationally connected to the temperature metering means (12), and also to other metering means (18), if necessary, in order to receive temperature information and to generate the information so, that the amount of evaporation of the metered object (1) will be obtained as a result.

* * * * *